(12) United States Patent
Bongs et al.

(10) Patent No.: US 6,395,507 B1
(45) Date of Patent: May 28, 2002

(54) PROCESS FOR DELAYING THE DEACTIVATION OF GLUTARYL AMIDASE DURING CATALYSIS WITH A THIOL

(75) Inventors: Jürgen Bongs, Wiesbaden; Johannes Meiwes, Idstein; Wolfgang Kruse, Hofheim; Klaus-Peter Koller, Bad Soden, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/578,684

(22) Filed: May 26, 2000

(30) Foreign Application Priority Data

May 28, 1999 (DE) .......................... 199 24 632

(51) Int. Cl.$^7$ .......................... C12P 35/00; C12N 9/96; C12N 9/14; C12N 9/80
(52) U.S. Cl. .......................... 435/47; 435/188; 435/228; 435/195
(58) Field of Search .......................... 435/47, 228, 188, 435/195

(56) References Cited

U.S. PATENT DOCUMENTS

| | | | |
|---|---|---|---|
| 4,990,444 A | | 2/1991 | Aretz et al. .................... 435/15 |
| 5,030,571 A | * | 7/1991 | Best et al. .................... 435/227 |
| 5,332,663 A | | 7/1994 | Battistel et al. ............... 435/51 |
| 5,766,881 A | | 6/1998 | Aretz et al. ................. 435/69.1 |
| 5,830,743 A | | 11/1998 | Koller et al. ............... 435/227 |

FOREIGN PATENT DOCUMENTS

| | | |
|---|---|---|
| EP | 0 275 901 B1 | 7/1988 |
| EP | 0 504 798 B1 | 9/1992 |
| EP | 0 525 861 B1 | 2/1993 |
| EP | 0 708 180 A2 | 4/1996 |
| ES | 2 093 555 A1 | 12/1996 |

OTHER PUBLICATIONS

Fernandez–Lafuente et al., Tetrahedron Letters, vol. 38, No. 26, pp. 4693–96, 1997.*
P. Golini et al., "Immobilization of D–amino acid oxidase from different yeasts: Characterization and application . . . ," *Enzyme Microb. Technol.*, 17:324–329 (1995).
Y. Yang et al., "Kinetics of inhibition of aminoacylase activity by dithiothreitol or 2–mercaptoethanol," *Int. J. Peptide Protein Res.*, 48:532–538 (1996).
D. Bianchi et al., "Immobilization of glutaryl–7–ACA acylase on aminoalkylated polyacrylic supports," *Enzyme Microb. Technol.*, 20:368–372 (1997).
W. Kördel et al., "Chemical Investigations on Pig Kidney Aminoacylase," *Biochimica et Biophysica Acta*, 445:446–457 (1976).
E. Battistel et al., "Purification and Stability of Glutaryl–7–ACA Acylase from *Pesudomonas sp.*," *Applied Biochemistry and Biotechnology*, 69:53–67 (1998).

* cited by examiner

Primary Examiner—David M. Naff
Assistant Examiner—Mike Meller
(74) Attorney, Agent, or Firm—Finnegan, Henderson, Farabow, Garrett, & Dunner, L.L.P.

(57) ABSTRACT

A process is provided for delaying the deactivation of glutaryl amidase during catalysis. The amidase is, after maximum conversion of a substrate, separated off by filtration and can be reused in a subsequent reaction batch. In each reaction cycle, the amidase loses activity. The inactivation of the amidase can be delayed by bringing it into contact with a thiol during the reaction. The thiol is preferably 2-mercaptoethanol or cysteine.

12 Claims, 1 Drawing Sheet

Fig. 1: Reaction scheme for the enzymatic synthesis of 7-ACS
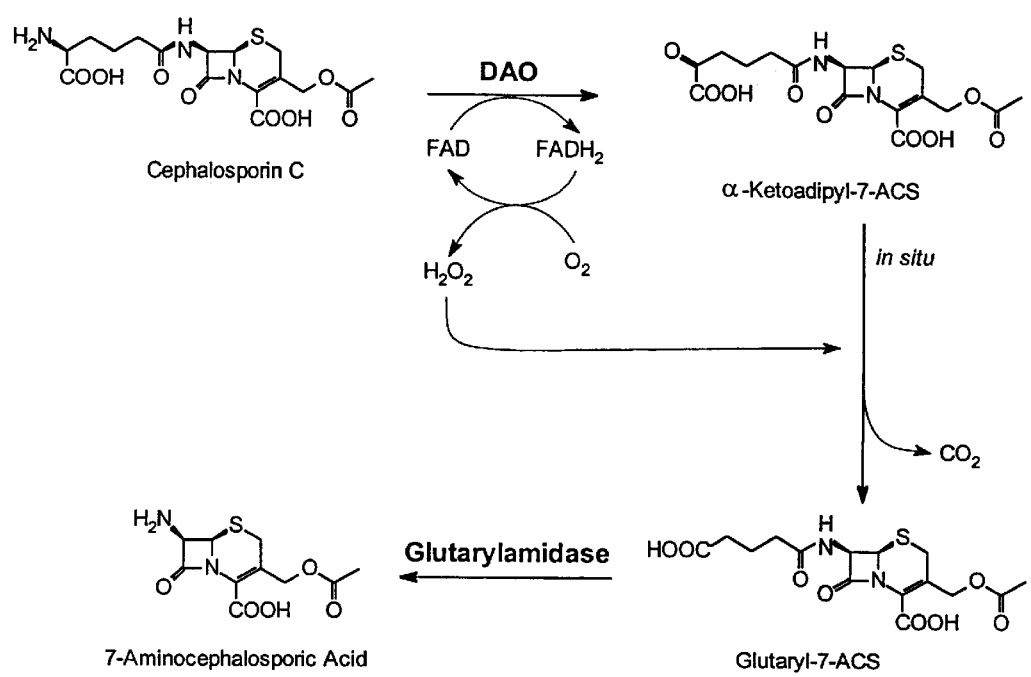

PROCESS FOR DELAYING THE DEACTIVATION OF GLUTARYL AMIDASE DURING CATALYSIS WITH A THIOL

The present invention relates to a process for delaying the deactivation of glutaryl amidase during enzyme catalysis.

7-Aminocephalosporic acid is of great commercial interest for the production of semisynthetic cephalosporin antibiotics.

The enzymatic synthesis of the antibiotic precursor 7-aminocephalosporic acid (7-ACS) is—as shown in FIG. 1—carried out in two reaction steps. Cephalosporin C is initially oxidized by action of D-amino acid oxidase (DAO) to α-ketoadipyl-7-ACS. In the next step, this compound is hydrolyzed to 7-ACS by glutaryl amidase (GAE).

The synthesis is carried out with the enzymes DAO and GAE, which are generally immobilized on supports and which are, after the reaction has ended, separated off from the solution of the product and can be reused for the next batch. However, if the catalyst is used repeatedly, the enzymes are deactivated, which is equivalent to enzyme consumption.

From the literature, it is known that structure-changing oxidations of proteins can be suppressed by using thiol reagents, such as, for example, 2-mercaptoethanol (P. Golini et al., *Enzyme and Microbial Technology* 17 (1995) 324–329; *Int J. Peptide Protein Res.* 48 (1996) 532–538).

DAO, for example, can be regenerated using thiols. The flavoprotein DAO catalyzes the stereospecific deamination of D-amino acids to the corresponding α-keto acids and ammonium, for example, as shown in FIG. 1, the conversion of cephalosporin C to α-ketoadipyl-7-ACS. α-Ketoadipyl-7-ACS decarboxylates in situ to glutaryl-7-ACS (G-7-ACS) (P. Golini et al., *Enzyme and Microbial Technology* 17 (1995) 324–329). In industry, the enzyme is frequently not employed in soluble form but immobilized by binding to polymers, such as, for example, amino-alkylated polymers or oxirane-activated polymers. Thus, after the reaction, the enzyme catalyst can be separated off by filtration, thus being available for reuse. The immobilized DAO catalyst suffers partial inactivation. When the enzyme catalyst, which has already been used once, is reemployed in a further reaction under otherwise identical conditions, the reaction time required for maximum conversion of the substrate is longer. This prolongation of the reaction time, which occurs on each reuse, is a measure of the stability of the catalyst in the preparation process of G-7-ACS. The extent of the change of the reaction time to maximum substrate conversion, determined over a plurality of production cycles, is referred to as operational stability. The operational stability of immobilized DAO can be improved by separating off the enzyme catalyst from the reaction mixture after the reaction by filtration, and treating it with a thiol, for example 2-mercaptoethanol. DAO contains some easily oxidizable sulfhydryl groups, predominantly as functional groups of the cysteine amino acids of the protein. The action of 2-mercaptoethanol is based on the reducing action of the thiol on the oxidation-sensitive sulfhydryl groups of the cysteines. The regeneration of these oxidized sulfhydryl groups results in a considerable improvement in operational stability. In the particular case of DAO, regeneration has to be carried out after separation of the enzyme from the reaction mixture, because $H_2O_2$ is formed during the enzyme catalysis. As a strong oxidizing agent, this would inactivate any added thiol.

Addition of thiol may also result in a reduction in the activity of proteins. This effect, too, can be explained by the presence of cysteine radicals. One example for this is aminoacylase. Aminoacylase is a dimeric enzyme having one $Zn^{2+}$ atom per subunit. Each subunit of the enzyme contains two cysteine SH groups and two disulfide bonds. The chemical modification of the SH groups, such as the breaking of the disulfide bonds, can result in an inactivation of the enzyme. It has been demonstrated that the activity of aminoacylase is reduced by addition of 2-mercaptoethanol, whereas, when the 2-mercaptoethanol is removed by dialysis or gel filtration, the original enzyme activity can be reestablished almost completely (W. Kördel and F. Schneider, *Biochem. Biophys. Acta* 445 (1976) 446–457).

Since the action of the thiol is apparently mediated by the oxidation or reduction of sulfhydryl groups of cysteine radicals, the addition of thiols to enzymes which are known not to contain any cysteine radicals should consequently not result in any change of the enzyme activity.

During repeated use of GAE in catalytical conversions of the catalyst, the enzyme is, as described at the outset for the synthesis of 7-ACS (cf. FIG. 1), deactivated, which corresponds to a consumption. The stability of the catalyst correlates with important production costs of the process, such as the time required, the waste produced, and the costs of the catalyst. A process that is comparable to the process described above for DAO and which is suitable for stabilizing GAE or increasing its operational stability has hitherto not been disclosed. The enzyme GAE comprises two peptide chains (protein A and B). The interaction of the chains is via hydrogen bonds and hydrophilic and hydrophobic interactions of protein domains.

It is an object of the present invention to provide a process for delaying the deactivation of glutaryl amidase during enzyme catalysis.

As can be seen from the amino acid analysis (Table 1), GAE lacks the amino acid cysteine. Thus, the use of thiol reagents for stabilization should not result in any enhanced operational stability of this biocatalyst. Contrary to expectation, it was possible to experimentally prove the opposite. In the case of GAE, the addition of various thiol-containing reagents, for example 2-mercaptoethanol or cysteine, resulted in a drastic increase in operational stability, depending on the concentration.

Accordingly, the object of the present invention is achieved by a process for delaying the inactivation during enzyme catalysis of GAE, comprising bringing the enzyme into contact with at least one thiol. The enzyme can optionally be present in free or supported form. A preferred support is, for example, an oxirane-activated polyacrylate.

Thiol or mercaptan is understood as meaning a chemical compound such as 2-mercaptoethanol, glutathione, or the amino acid cysteine, the common feature of which is that they contain a thiol group (—SH) in the molecule.

Supported GAE consists of the enzyme catalyst GAE which is attached, for example, to oxirane-activated or else amino-alkylated polyacrylates (=supports). A process for preparing supported GAE is described in D. Bianchi et al., *Enzyme and Microbiological Technology* 20 (1997) 368–372. Examples of supports are EUPERGIT® (oxirane containing polymer), AMBERLITE® XAD7 (nonionic polymeric adsorbent), and DUOLITE® A365 (ion-exchange resin)(all from Röhm and Haas).

EXAMPLES

A practical application of enzyme catalysis with GAE is the preparation of 7-ACS from G-7-ACS (cf. FIG. 1). The enzyme catalysis was carried out as follows:

The substrate G-7-ACS was, in a concentration of 40 mM, reacted at 40° C. and pH 8.3 in a reaction volume of 120 ml with the immobilized GAE (from Pseudomonas diminuta). With the aid of an automated peripheral system, it was possible to measure process-relevant parameters (pH, temperature) on-line and to control them using a suitable control system. Thus, the pH shift into the acidic range, which occurred as a result of the reaction, was neutralized by autotitration with base. The rate of the addition of base correlated with the rate of reaction and could be used as a measure of the degree of conversion of the substrate (G-7-ACS). PC-assisted data processing permitted the on-line determination of the conversion and gave the termination criterion of the reaction. The reaction was terminated when maximum conversion was reached. That maximum conversion had been reached became apparent in that it was no longer necessary to add base. Once maximum conversion had been reached, the catalyst was filtered off from the solution of the product, and fresh substrate solution was then added. The reaction times of the individual successive reactions (=batches) could be plotted as a function of the batches. Via linear regression, a gradient (=X coefficient (min/batch)) was obtained which could be used as a measure of catalyst deactivation. The lower this value, the higher the operational stability of the catalyst.

In one embodiment of the invention, the thiol used is 2-mercaptoethanol. This is preferably employed in a concentration range of 1 to 100 mM.

In another embodiment of the invention, it is possible to add, as thiol, cysteine, preferably in the range 1 to 100 mM.

The thiol can be used continuously, i.e., over the course of the reaction, or batchwise, i.e., in between the enzymatic reactions. The successful use can be seen from the reduced reaction time required for reaching quantitative conversion of the substrate.

The concentration of the substrate G-7-ACS was, for example, varied in a range between 5 and 500 mM. It was preferably employed in a concentration range of from 20 to 80 mM. Over wide ranges, the result of the reaction was in principle independent of the reaction volume employed.

The use of a thiol according to any of the processes described is possible to delay the deactivation of GAE.

Example 1

Reaction Time to Quantitative Conversion as a Function of the Batch Number without or with Cysteine In a plurality of test series, cysteine as thiol reagent was added in various concentrations to the substrate solution, and the reaction was carried out as described. As can be seen from the table below, the gradient and thus, the X coefficient, decreased with increasing cysteine concentration. Assuming linear deactivation over the reactions carried out, it was possible to determine, for each series of measurements, the number of batches possible until the reaction time doubled. The values are shown in the table below. A considerable increase in operational stability is evident in those cases where the reaction batch additionally contained cysteine, and by the increase in the number of individual reaction batches which could be run until the reaction time to maximum substrate conversion had doubled.

The reaction parameters were chosen as follows:

| Reaction parameters: | |
|---|---|
| $V_R$ = | 120 ml |
| T = | 40° C. |
| pH = | 8.3 (Ammonia 1.66%) |
| Amount (G-7-ACS) = | 40 mM (KPP 100 mM) |
| Amount (Cysteine)$_{in\ the\ substrate}$ = | variable |
| Amount (GAE) = | 500 U |

Table for Example 1: Reaction time to quantitative conversion as a function of the batch number without or with cysteine

| | without cysteine | with cysteine, 1 mM | with cysteine, 6 mM | with cysteine, 8 mM | with cysteine, 10 mM |
|---|---|---|---|---|---|
| X coefficient (min/batch) | 0.414 | 0.131 | 0.077 | 0.046 | 0.016 |
| Number of batches until the reaction time had doubled (for linear deactivation) (–) | 36 | 114 | 195 | 326 | 938 |

Comparison of the X coefficient (i.e., the increase in time per batch) for reaching quantitative conversion or the number of batches until the reaction time had doubled, as a function of the cysteine concentration in the substrate solution Example 2

Reaction Time to Quantitative Conversion as a Function of the Batch Number without or with Mercaptoethanol The use of 2-mercaptoethanol as thiol reagent leads to an increase in the operational stability of GAE. The table below shows the comparison of the test runs with and without 2-mercaptoethanol. With respect to the stabilization of operational stability, the results for 2-mercaptoethanol are comparable to those of cysteine.

The reaction parameters were chosen as follows:

| Reaction parameters: | |
|---|---|
| $V_R$ = | 120 ml |
| T = | 40° C. |
| pH = | 8.3 (Ammonia 1.66%) |
| Amount (G-7-ACS) = | 40 mM |
| Amount (GAE) = | 500 U |
| Amount (Mercaptoethanol) = | 1 µl/ml |

Table for Example 2: Reaction time to quantitative conversion as a function of the batch number without or with mercaptoethanol

|  | without mercaptoethanol | with mercaptoethanol, 1 μl/ml |
|---|---|---|
| X coefficient (min/batch) | 0.44 | 0.08 |
| Number of batches until the reaction time had doubled (for linear deactivation) (−) | 41 | 225 |

Comparison of the X coefficient (i.e., the increase in time per batch, i.e., the gradient) for reaching quantitative conversion without or with mercaptoethanol The cloning of the gene from Pseudomonas and the expression in *E. coil* has been described, for example, in EP-P-0504798 (U.S. Pat. No. 5,830,743) and EP-A-0708180 (U.S. Pat. No. 5,766,881). The use of microorganisms or enzymes of these for preparing 7-ACS is disclosed in EP-A-0275901 (U.S. Pat. No. 4,990,444) and EP 0525861 B1 (U.S. Pat. No. 5,332,663). A purification process for the enzyme, using an overproducing *E. coli* strain, is described in D. Bianchi et al., *Enzyme and Microbiological Technology* 20 (1997) 368–372.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

TABLE 1

Amino acid analysis protocol of GAE

| Radical | Number | Mole percent |
|---|---|---|
| A = Ala | 85 | 11.806 |
| B = Asx | 0 | 0.000 |
| C = Cys | 0 | 0.000 |
| D = Asp | 49 | 6.806 |
| E = Glu | 32 | 4.444 |
| F = Phe | 31 | 4.306 |
| G = Gly | 55 | 7.639 |
| H = His | 13 | 1.806 |
| I = Ile | 23 | 3.194 |
| K = Lys | 11 | 1.528 |
| L = Leu | 57 | 7.917 |
| M = Met | 14 | 1.944 |
| N = Asn | 30 | 4.167 |
| P = Pro | 55 | 7.639 |
| Q = Gln | 34 | 4.722 |
| R = Arg | 52 | 7.222 |
| S = Ser | 37 | 5.139 |
| T = Thr | 45 | 6.250 |
| V = Val | 49 | 6.806 |
| W = Trp | 16 | 2.222 |
| Y = Tyr | 32 | 4.444 |
| Z = Glx | 0 | 0.000 |

TABLE 1-continued

Amino acid analysis protocol of GAE

| Radical | Number | Mole percent |
|---|---|---|
| A + G | 140 | 19.444 |
| S + T | 82 | 11.389 |
| D + E | 81 | 11.250 |
| D + E + N + Q | 145 | 20.139 |
| H + K + R | 76 | 10.556 |
| D + E + H + K + R | 157 | 21.806 |
| I + L + M + V | 143 | 19.861 |
| F + W + Y | 79 | 10.972 |

Sum for the entire sequence:
Molecular weight = 79685.47
Number of radicals = 720
Mean molecular weight per radical = 110.674
Charge = −18
Isoelectric point = 5.20
Extinction coefficient = 132000

What is claimed is:

1. A process for delaying the deactivation of glutaryl amidase during catalysis by said amidase in a substrate solution, comprising bringing the glutaryl amidase into contact with at least one thiol selected from the group consisting of 2-mercaptoethanol and cysteine.

2. The process of claim 1, wherein the glutaryl amidase is coupled to a polymeric support.

3. The process of claim 2, wherein the polymeric support is an oxirane-activated polyacrylate.

4. The process of claim 1, wherein said at least one thiol is 2-mercaptoethanol.

5. The process of claim 4, wherein the concentration of 2-mercaptoethanol is in the range from 1 to 100 mM.

6. The process of claim 1, wherein said at least one thiol is cysteine.

7. The process of claim 6, wherein the concentration of cysteine is in the range from 1 to 100 mM.

8. The process of claim 1, wherein, during the amidase catalysis, said at least one thiol is continuously present in the substrate solution.

9. The process of claim 8, wherein the glutaryl amidase is removed from the substrate solution and then brought into contact with said at least one thiol.

10. The process of claim 9, wherein the substrate of the amidase catalysis is glutaryl-7-aminocephalosporic acid.

11. The process of claim 10, wherein glutaryl-7-aminocephalosporic acid is in the concentration range from 5 to 500 mM.

12. A process for preparing 7-aminocephalosporic acid, comprising a) reacting glutaryl-7-aminocephalosporic acid with glutaryl amidase; and b) delaying the deactivation of said glutaryl amidase by bringing said glutaryl amidase into contact with at least one thiol selected from the group consisting of 2-mercaptoethanol and cysteine.

* * * * *